United States Patent [19]

Chaumet

[11] Patent Number: 4,757,824
[45] Date of Patent: Jul. 19, 1988

[54] METHOD AND APPARATUS FOR MONITORING RESPIRATION

[75] Inventor: Serge G. J. Chaumet, Paris, France

[73] Assignee: Kontron Holding A.G., Zurich, Switzerland

[21] Appl. No.: 897,476

[22] Filed: Aug. 15, 1986

[30] Foreign Application Priority Data

Aug. 21, 1985 [CH] Switzerland ............ 3588/85

[51] Int. Cl.⁴ .............................................. A61B 5/08
[52] U.S. Cl. .................................. 128/716; 128/671; 128/700; 128/723
[58] Field of Search ............... 128/670, 671, 700, 716, 128/721-723, 725

[56] References Cited

U.S. PATENT DOCUMENTS

| | | |
|---|---|---|
| 3,976,052 | 8/1976 | Junginger et al. |
| 3,994,284 | 11/1976 | Voelker |
| 4,279,257 | 7/1981 | Hochstein |
| 4,306,567 | 12/1981 | Krasner |
| 4,365,636 | 12/1982 | Barker |
| 4,403,215 | 9/1983 | Hofmann et al. |
| 4,422,458 | 12/1983 | Kravath |
| 4,449,537 | 5/1984 | Pross et al. |
| 4,580,575 | 4/1986 | Birnbaum et al. ............ 128/671 |

FOREIGN PATENT DOCUMENTS

| | | |
|---|---|---|
| 0029349 | 5/1981 | European Pat. Off. |
| 0048591 | 3/1982 | European Pat. Off. |
| 0082655 | 6/1983 | European Pat. Off. |
| 2192790 | 2/1974 | France |
| WO84/00227 | 1/1984 | PCT Int'l Appl. |
| 2060892 | 5/1981 | United Kingdom |

OTHER PUBLICATIONS

Sahakian et al., "A . . . Apnea Monitor", Conf. Proc. 10th Ann NW Bio. Eng. Conf., Hanover N.H., Mar. 1982, p. 151-156.

Y. Miyamoto et al., Med. & Biol. Eng. & Comp., vol. 19, pp. 638-644, (1981).

J. Almasi and O. Schmitt, IEEE Transactions on Biomedical Engineering, vol. 21, No. 4, pp. 264-273, (1974).

W. Tompkins et al., Medical Biological Engineering, vol. 9, pp. 771-712, (1971).

D. Cathignol, Med. & Biol. Eng. & Comput., vol. 16, pp. 459-470, (1978).

A. Wilson et al., Med. & Biol. Eng. & Comput., vol. 20, pp. 293-298, (1982).

Primary Examiner—Lee S. Cohen
Attorney, Agent, or Firm—Jon S. Saxe; Bernard S. Leon; Richard J. Mazza

[57] ABSTRACT

A method and an apparatus are provided for monitoring waveforms representing the respiration of a patient and for detecting waveforms having characteristics indicative of apnea. The method comprises processing a first electrical signal having a waveform representing the respiration of the patient and a second electrical signal representing the electrocardiogram of the patient.

In order to increase the reliability of apnea alarms and the accuracy of measuring apnea duration, the method comprises: comparing the amplitude of the first signal, or the amplitude of a signal obtained by transformation of the first signal, at the time of incidence of each QRS complex with a predetermined threshold value, resetting to zero the first signal or said signal obtained by transformation of the first signal in synchronism with the incidence of each QRS complex on the second signal, and triggering an alarm if the amplitudes of the first signal, or of said signal obtained by transformation thereof, at the said times do not exceed the threshold value over a predetermined interval of time, said alarm being indicative of apnea.

3 Claims, 12 Drawing Sheets

METHOD AND APPARATUS FOR MONITORING RESPIRATION

BACKGROUND OF THE INVENTION

This invention relates to an apparatus and a method of monitoring waveforms representing the respiration of a patient, and of detecting waveforms having characteristics indicative of apnea, this method comprising processing a first electrical signal having a waveform representing the respiration of the patient and a second electrical signal representing the electrocardiogram of the patient.

In the method of monitoring waveforms representing a patient's respiration, the reliability of apnea alarms (indicating cessation of respiration), accuracy of measurement of the duration of each apnea, and the sensitivity of the measuring system for detecting apnea, are greatly restricted by the presence of artefacts, which are synchronous with cardiac activity, on the wave of the signal representing the patient's respiration, this signal being produced, for example, by measuring the variation in the transthoracic impedance. In this case, the artefacts, known as cardiovascular artefacts, are due to the fact that the movement of the heart and the variation in blood flow produce a variation in the impedance of the rib cage.

If the respiratory signal wave did not contain the above artefacts, apnea could be detected, at least in principle, by monitoring the amplitude of the respiratory signal wave and by detecting the intervals in which said amplitude is below a predetermined threshold value. In actual fact, a method of this kind is not reliable, because the amplitude of the cardiovascular artefacts, which are present even in the case of apnea (an apnea should be indicated by a shallow respiration wave of practically zero amplitude), may very often exceed the selected detection threshold and may therefore erroneously be thought to indicate the presence of normal respiration. If a low detection threshold is selected, in fact, there is a risk of apnea occurring unnoticed. If, on the other hand, a high detection threshold is chosen, there is a risk of false apnea alarms being triggered when the respiratory signal is of low amplitude but not yet low enough to be an apnea. Since the cardiovascular artefacts may often have an amplitude equal to or even greater than that of the respiratory signal if the latter is shallow, the user of such a method finds it impossible to choose a suitable detection threshold to enable him to obtain reliable apnea indication and to measure the duration of such apnea accurately.

Fluctuations in the baseline of the respiratory signal and other interference signals frequently superimposed thereon also make reliable detection of apnea difficult.

The following methods have already been proposed to improve the reliability of apnea detection despite the presence of cardiovascular artefacts:

In a first known method (French patent application published under the No. 2,267,734), the interval of time corresponding to the period of the respiratory signal is compared with the interval between successive QRS complexes of the signal representing the patient's electrocardiogram. and if the difference between these intervals remains below a predetermined threshold value over a predetermined interval of time it is assumed that the apparently existing respiratory signal is in fact a cardiovascular artefact.

In a second known method (French patent application published under the number 2 192 790) the phase difference is measured between the respiratory signal and the signal representing the patient's electrocardiogram, and if this difference remains below a predetermined threshold value over a predetermined interval of time it is assumed that the apparently existing respiratory signal is in fact a cardiovascular artefact.

The above two known methods have the following disadvantages:

Since cardiac artefacts are often at the limit of detection, their random detection eludes the frequency or phase comparison means and results in respiration being thought to be normal, with no apnea detection.

In a third known method (UK patent application No. 2 060 892), a signal is formed which represents the first derivative of the respiratory signal with respect to time and the slope of this signal is examined at intervals of time corresponding to the intervals of time between successive QRS complexes of the signal representing the patient's electrocardiogram, and if this slope assumes a negative value in the interval during which it is examined, and if this occurs a plurality of consecutive times, it is assumed that the apparently existing respiratory signal is in fact a cardiovascular artefact.

This third known method has the following disadvantages:

it is sensitive to the polarity of the signal and does not operate if the electrodes are not correctly placed, it is sensitive to noise of any kind and, in particular, a very noisy random signal may be classed as apnea because it has every likelihood of having negative slopes in the examination interval, it takes into account the form of the artefact at the time of incidence of the QRS complex, such form is however not identical from one patient to another and depends on the positioning of the electrodes.

This method may therefore be inoperatve on certain patients.

SUMMARY OF THE INVENTION

The primary underlying object of the invention described hereinafter is to provide a method of and apparatus for performing the same whereby the disadvantages of the above-described known methods and apparatus can be at least partially eliminated so as to give reliable apnea alarms and enable the duration of each apnea to be measured with greater accuracy and sensitivity despite the presence of cardiovascular artefacts on the respiratory signal wave. Another object is to provide a method and apparatus of this kind at the lowest possible price and in the smallest possible size so that their incorporation in a respiration monitoring system will not excessively increase its cost.

DESCRIPTION OF THE INVENTION

According to the present invention, the above objectives are realized with a method involving processing a first electrical signal having a waveform representing the respiration of a patient and a second electrical signal representing the electrocardiogram of the patient, which method comprises (a) comparing the amplitude of the first signal or of the amplitude of a signal obtained by transformation of the first signal, at the time of the incidence of each QRS complex with a predetermined threshold value, (b) resetting to zero the first signal or said signal obtained by transformation thereof in synchronism with the incidence of each QRS complex on the second signal, and (c) triggering an alarm if the amplitudes of the first signal or of said signal obtained by transformation thereof at the said times do not exceed the threshold value over a predetermined interval of time, this alarm being indicative of apnea.

In the preferred embodiment, the method according to the invention comprises (a) forming a third signal by transformation of the first signal, (b) forming a fourth signal by transformation of the third signal, (c) comparing the amplitude of the fourth signal at the time of the incidence of each QRS complex with a predetermined threshold value, (d) resetting the fourth signal to zero in synchronism with the incidence of each QRS complex on the second signal, and (e) triggering an alarm if the amplitudes of the fourth signal at the said times do not exceed the threshold value over a predetermined interval of time, said alarm being indicative of apnea.

A further preferred embodiment of this method comprises (a) forming a third signal which represents the first derivative of the first signal with respect to time, (b) forming a fourth signal which represents the integral of the third signal over first integration intervals, each of these intervals corresponding to the interval between two successive QRS complexes of the second signal, (c) comparing the amplitude of the fourth signal at the time of the incidence of each QRS complex which marks the end of one of the said integration intervals with a predetermined threshold value, (d) resetting to zero the fourth signal in synchronism with the incidence of each QRS complex on the second signal, and (e) triggering an alarm if the amplitudes of the fourth signal at the said times do not exceed the threshold value over a predetermined interval of time, said alarm being indicative of apnea.

The invention also relates to apparatus for monitoring the respiration of a patient, comprising means for forming a first electrical signal having a waveform representing the respiration of the patient and a second electrical signal representing the electrocardiogram of the patient, and means for detecting waveforms of the first signal having characteristics indicative of apnea. According to the invention, this apparatus comprises:

(a) means for deriving a third signal by conversion of the first signal, (b) means for forming a fourth signal by conversion of the third signal, (c) means for comparing the amplitude of the fourth signal at the time of the incidence of each QRS complex with a predetermined threshold value, (d) means for resetting the fourth signal to zero in synchronism with the incidence of each QRS complex on the second signal, and (e) means for triggering an alarm if the amplitudes of the fourth signal at the said times do not exceed the threshold value over a predetermined interval of time, said alarm being indicative of apnea.

One preferred embodiment of the apparatus according to the invention comprises (a) means for forming a third signal representing the first derivative of the first signal with respect to time, (b) means for forming a fourth signal representing the integral of the third signal over first integration intervals, each of said intervals corresponding to the interval between two successive QRS complexes of the second signal, (c) means for comparing the amplitude of the fourth signal at the time of incidence of each QRS complex which marks the end of one of said integration intervals with a predetermined threshold value, (d) means for resetting the fourth signal to zero in synchronism with the incidence of each QRS complex on the second signal, and (e) means for triggering an alarm if the amplitudes of the fourth signal at said times do not exceed the threshold value over a predetermined interval of time, said alarm being indicative of apnea.

The advantages obtained by performing the method according to the invention and by using apparatus according to the invention are as follows:

considerable improvement of apnea alarm reliability, increased sensitivity of the measuring system for apnea detection, a considerable increase in the accuracy of measurement of the duration of each apnea, and the simplicity and low cost of the means required for performing the method and for constructing the apparatus according to the invention.

BRIEF DESCRIPTION OF THE DRAWINGS

Exemplified embodiments of the method and of the apparatus according to the invention are described below with reference to the accompanying drawings.

DETAILED DESCRIPTION OF THE DRAWINGS

Figure 1:
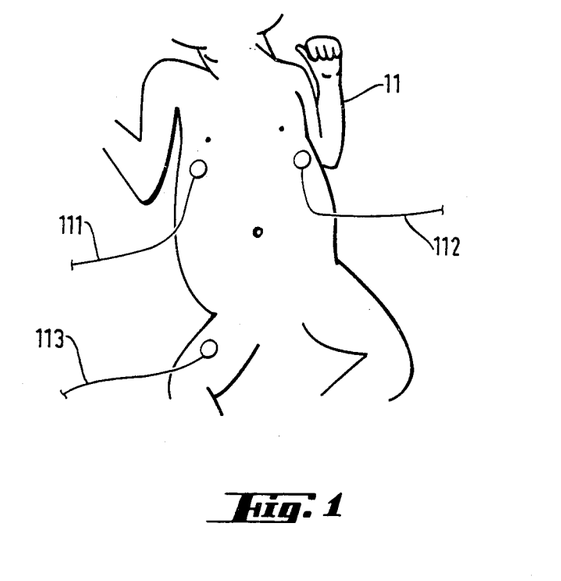
FIG. 1 shows the positioning of electrodes to produce the respiratory signal and the signal representing a patient's electrocardiogram.

FIG. 1 shows the positioning of electrodes 111 and 112 to produce a signal representing a patient's respiration and a signal representing a patient's electrocardiogram, the patient, for example, being a newborn baby. In the example shown in FIG. 1, these two signals are produced by the same set of electrodes. Within the scope of this invention each of these signals may, however, be produced independently of one another by separate means.

An optional third electrode 113 can be used as a potential reference.

The electrodes shown in FIG. 1 enable the respiratory signal to be produced by measuring the transthoracic impedance. This signal may also be produced by other means, e.g., by a thoracic strain gauge, or a displacement or acceleration pick-up, an acoustic pick-up, or a pneumatic pick-up for detecting the variation in the pressure of a pneumatic mattress, etc.

Figure 2:
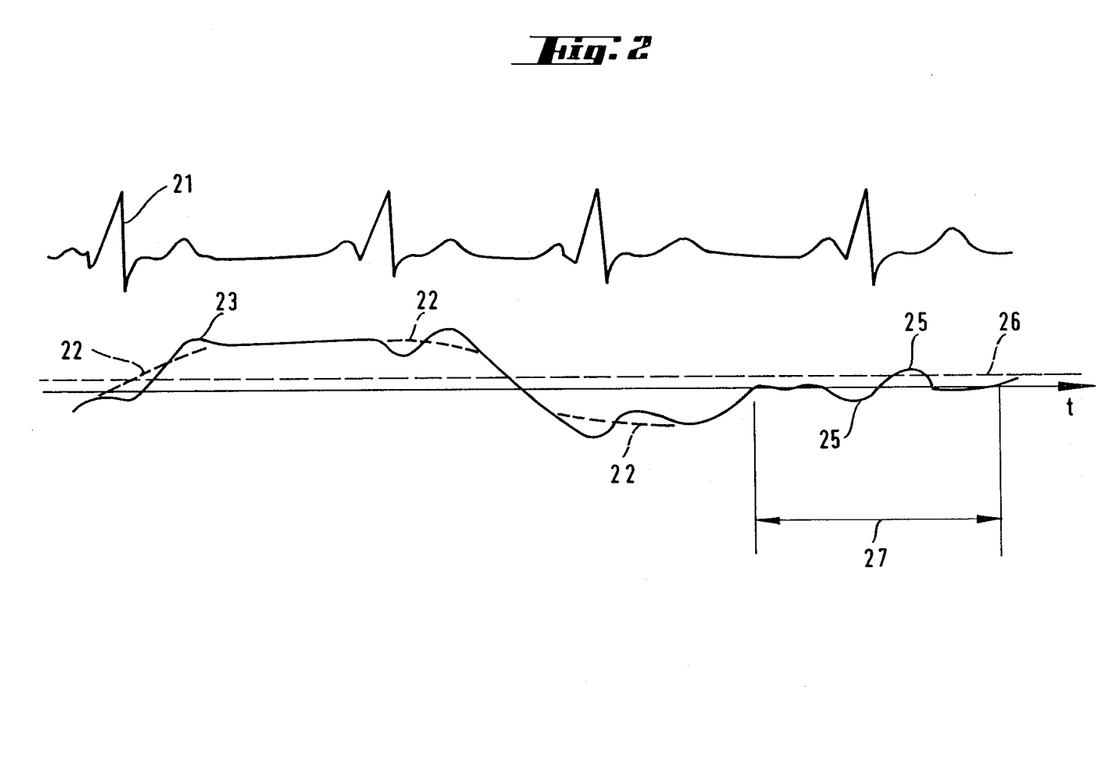
FIG. 2 shows waveforms representing the patient's electrocardiogram and respiratory signal.

FIG. 2 shows typical waveforms of the following signals, which are obtained simultaneously from a patient:

a wave 21 representing the electrocardiogram of the patient 11, a wave 22 representing the patient's respiration in the ideal case in which said wave has no cardiovascular artefacts, and a waveform 23 representing the respiratory signal when the same contains cardiovascular artefacts.

In the interval of time 27 in FIG. 2, the wave 22 of the pure respiratory signal has a practically zero amplitude, and this corresponds to apnea. However, the wave 23 has an amplitude which exceeds a detection threshold 26 because it contains a cardiovascular artefact represented by the portion 25 of the wave 23. This artefact therefore prevents detection of the apnea by means of the detection threshold 26 and leads to the interpretation of normal respiration being present in the interval 27. The following difficulties are met in the attempt to detect apnea by comparing the amplitude of the respiratory signal 23 with a detection threshold 26:

if the threshold chosen is low there is a risk of apnea not being detected (this is the case in the interval 27 in FIG. 2), if, on the other hand, the threshold selected is high, there is a risk of false apnea alarms being triggered in the event of a normal respiratory signal of low amplitude.

In every case, i.e., irrespective of the selected threshold 26, the presence of cardiovascular artefacts interferes with the accuracy of measurement of the real time of respiratory pauses (apnea) and makes it difficult for the user to select a suitable detection threshold 26 (by adjusting the sensitivity), because the respiratory signal amplitude varies not only from one patient to another but also with time in the case of one and the same patient. These difficulties are obviated by the use of the methods according to the invention as described below.

Figure 3:
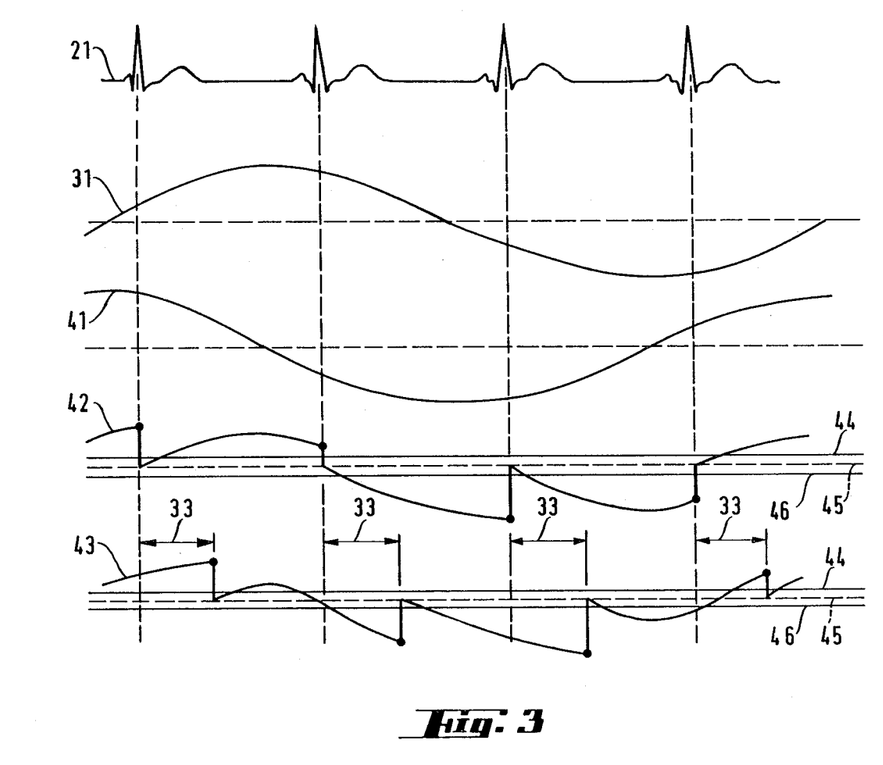
FIG. 3 illustrates a first embodiment of the method according to the invention by reference to a number of typical waveforms of the signals involved, in the case of a normal respiratory signal without apnea.

In the case of normal respiration without apnea, a first embodiment of the method according to the invention is illustrated by the waveforms shown in FIG. 3, in which the time axes are denoted by broken horizontal lines. This method is carried out with two signals produced simultaneously from one patient: the signal 21 representing the electrocardiogram and the respiratory signal 31. The signal 31 contains cardiovascular artefacts but they have no appreciable effect on the result of the method in the case shown in FIG. 3, and in order to simplify the representation the representation of the signal 31 in FIG. 3 does not show such artefacts.

Figure 4:
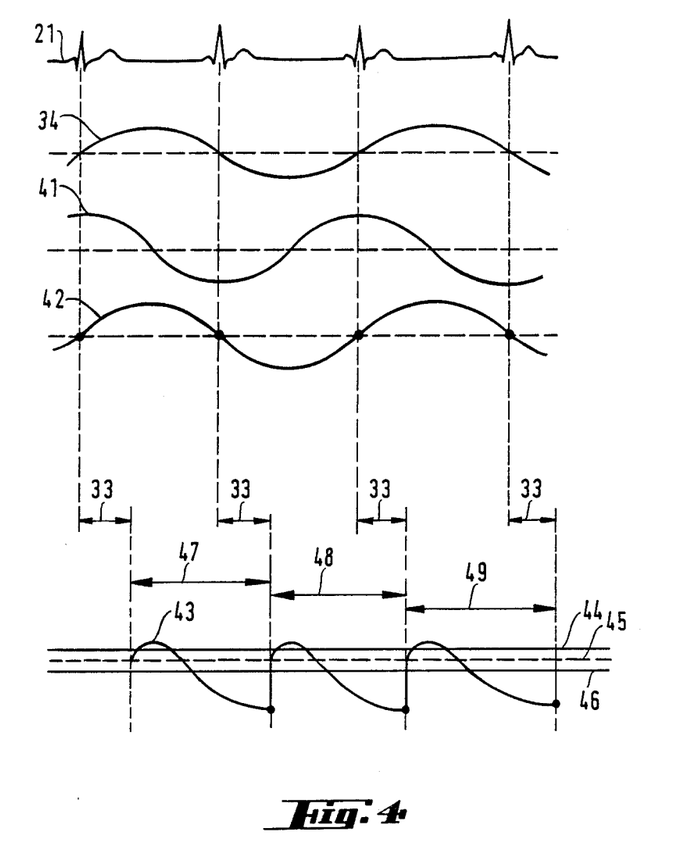
FIG. 4 illustrates a preferred version of the first embodiment of the method according to the invention in the case of a respiratory signal without apnea but extremely unfavorable.

In the method according to the invention, a signal 41 is formed whose waveform represents the first derivative of the waveform of the respiratory signal 31 with respect to time, and a signal 42 is formed whose waveform represents the integral of the signal 41 over integration intervals, each of said intervals being defined by the interval between two successive QRS complexes of the signal 21, with resetting to zero on the incidence of each QRS complex. In FIGS. 3 and 4 the incidence of these complexes denoted by broken vertical lines.

The amplitude of the signal 42 at the time of incidence of each QRS complex marking the end of one of the integration intervals is compared with a threshold value 44 for the amplitudes with a positive polarity and with a threshold value 46 for the amplitudes of negative polarity. If the amplitudes of the signal 42 at the said times do not exceed the threshold values 44 and 46 respectively over a predetermined interval of time, an alarm indicative of apnea is triggered.

The above-described method has the following advantages:

the use of the first derivative with respect to time (formation of signal 41), on the one hand, and resetting to zero at the end of each integration interval (on formation of signal 42), on the other hand, make the amplitude of the signal 42 insensitive to the fluctuations (drift) of the base line of the respiratory signal 31.

the integration operation applied to the signal 41 also comprises a low-pass filtration which reduces the influence of other artefacts (other than cardiovascular artefacts) and reproducibility errors.

The above-described method, although quite usable in general, becomes inoperative in the specific case shown in FIG. 4 in which the frequency of the respiratory signal 34 is exactly half the frequency of the ECG signal 21 and, in addition, signal 34 has an unfavourable phase ratio with respect to signal 21. In this specific case, the amplitude of signal 42 always assumes the value zero at the end of each integration interval and leads to the interpretation that apnea is present. To obviate this difficulty, in a preferred version of the method described above, a signal 43 is additionally formed, the waveform of which represents the integral of the signal 41 over integration intervals 47, 48, 49, etc., each of which is offset by an interval 33, e.g., 200 milliseconds (ms), with respect to one of the integration intervals used for forming the signal 42, and the amplitude of the signal 43 at the time marking the end of each of these integration intervals 47, 48, 49, etc., is compared with the predetermined threshold values 44 and 46 respectively. In this preferred version of the first embodiment of the method according to the invention the apnea alarm is triggered only if the amplitudes of the signal 42 and the amplitudes of the signal 43 at the end of the respective integration intervals do not exceed the threshold value over a predetermined interval of time, e.g., 3 seconds.

In the extremely unfavourable case shown in FIG. 4, the amplitudes of the signal 43 at the end of the integration intervals exceed the threshold value 46 and reliably prevent a false apnea alarm from being triggered.

In the more general and frequent case illustrated in FIG. 3, the values of the amplitudes of the signals 42 and 43 at the end of the respective integration intervals exceed the threshold values 44 and 46, respectively, and reliably prevent a false apnea alarm from being triggered.

Figure 5:
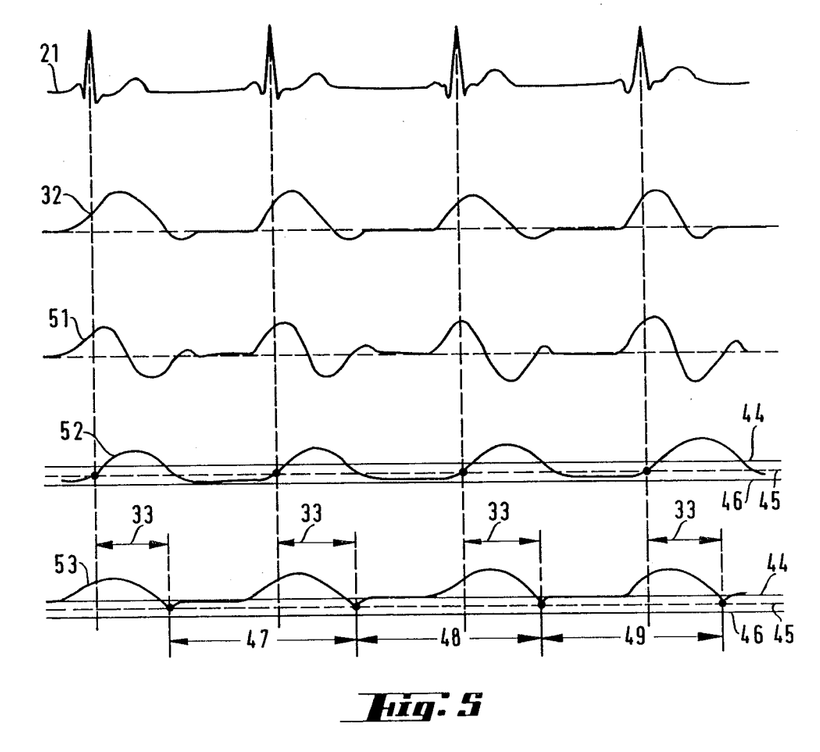
FIG. 5 illustrates a method according to the invention similar to that described with reference to FIG. 4 but in the case of an apnea in the presence of cardiovascular artefacts.

In the case of an apnea in the presence of cardiovascular artefacts, the first embodiment of the method according to the invention is illustrated by the waveforms shown in FIG. 5, in which the time axes are denoted by broken horizontal lines. As before, this method is performed by means of two signals produced simultaneously from one patient: signal 21 representing the ECG and a signal 32 obtained with the same means used to produce the respiratory signal 31 in FIG. 3. Since the signal 32 represents an apnea (absence of respiration), its waveform represents practically only cardiovascular artefacts.

In the method according to this invention, a signal 51 is formed whose waveform represents the first derivative of the waveform of the signal 32 with respect to time, and a signal 52 is formed whose waveform represents the integral of the signal 41 over integration intervals, each of said intervals being defined by the interval between two successive QRS complexes of the signal 21, with resetting to zero on the incidence of each QRS complex. In FIG. 5 the incidence of each of these complexes is denoted by a vertical broken line.

The amplitude of the signal 52 at the time of incidence of each complex QRS marking the end of one of the integration intervals is compared with the threshold value 44 for the positive polarity amplitudes and with the threshold value 46 for the negative polarity amplitudes.

FIG. 5 shows that at the above-defined times in an apnea interval the amplitudes of the signal 52 are less than the threshold values 44 and 46. According to the first embodiment of the method according to the invention, an alarm is triggered which indicates an apnea if said amplitudes remain below said thresholds over a predetermined interval of time.

In order to improve the reliability of the method according to the invention, in the preferred version thereof described above, there is also formed a signal 53, whose waveform represents the integral of the signal 51 over integration intervals 47, 48, 49, etc., each of which is offset by the interval 33 with respect to one of the integration intervals used for the formation of the signal 52, and the amplitude of the signal 53 at the time marking the end of each of these integration intervals 47, 48, 49, etc., is compared with the threshold values 44 and 46, respectively. FIG. 5 shows that in an apnea interval the amplitudes of the signals 52 and 53 at the end of the respective integration intervals are less than the threshold values 44 and 46 respectively. According to the preferred version of the first embodiment of the method according to the invention, an alarm indicative of an apnea is triggered if said amplitudes remain below said threshold over a predetermined interval of time.

Figure 6:
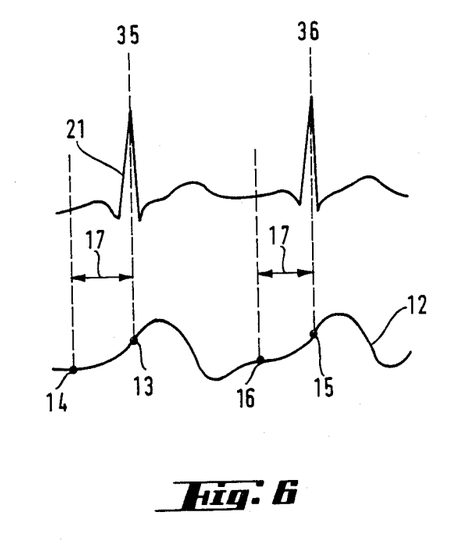
FIG. 6 shows typical cardiovascular artefact waveforms.

The efficiancy of the methods according to the invention is based on certain properties of the cardiovascular artefacts. As shown in FIG. 6, the waveform 12 of a signal representing cardiovascular artefacts may have any arbitrary form but is generally fairly periodic, in synchronism with the signal 21 representing the ECG and repetitive in its form. As shown in FIG. 6, the waveform 12 of the signal representing a cardiovascular artefact resumes the same amplitude value for each time of its period. Thus the amplitude of the point 13 of the wave 12 on the incidence of a QRS complex of signal 21 at time 35 is the same as that of point 15 at time 36 on the incidence of the next QRS complex. The points 14 and 16 prior to the points 13 and 15, respectively, of the wave 12 and which are separated from these points by intervals of time 17, also have the same amplitude. The latter characteristic of the waveform of cardiovascular artefacts is in fact an adequate condition for the methods according to the invention to allow reliable apnea detection and accurate measurement of apnea duration during monitoring of a patient's respiration.

Figure 7:
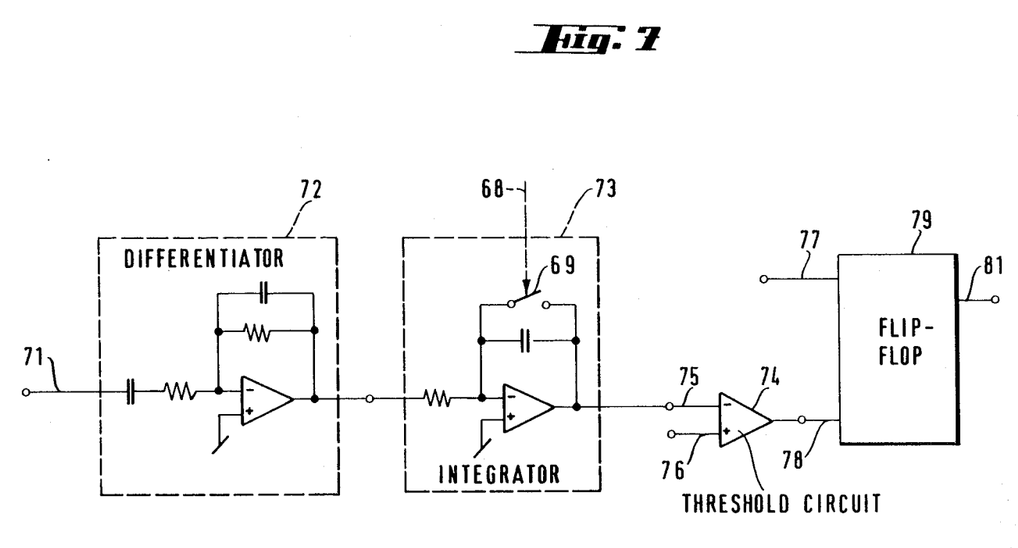
FIG. 7 shows a first embodiment of an electronic system for performing the method according to the invention.

FIG. 7 shows a first embodiment of an electronic system for performing a method according to the invention. This system comprises the series connection of the following circuits: a differentiating circuit 72, an integrating circuit 73, a threshold detector 74 and a bistable type D flip-flop 79.

The respiratory signal is applied to the input 71 of the differentiating circuit 72. At its output the latter delivers a signal representing the first derivative of the respiratory signal with respect to time. This signal is applied to the input of the integrator 73. At its output the latter delivers a signal representing the integral of the signal applied to its input over integration intervals each corresponding to the interval between two successive QRS complexes of the patient's ECG. The integrator 73 is reset to zero on the incidence of each QRS complex by the closing of a switch 69 for a short time. This closing operation is controlled by a signal representing the respective QRS complex, said signal being derived from the signal representing the ECG by means of a suitable detector circuit. In FIG. 7, the control for closing switch 69 is represented by a broken line 68. The signal delivered at the output of integrator 73 is applied to a first input 75 of the threshold detector 74. A voltage corresponding to a predetermined threshold value is applied to a second input 76 of the threshold detector 74. According to the result of the comparison of the signals applied to these inputs, the threshold detector 74 outputs a signal corresponding to a logic 1 or 0. This signal is applied to the input D of the flip-flop circuit 79 via line 78. On the incidence of each QRS complex a signal corresponding thereto is applied via a line 77 to a second input of the flip-flop circuit 79. This trigger input is the one receiving the clock pulses when the trigger circuit is used in digital circuits. The output signal of the trigger circuit 79 is delivered over line 81. This output signal is applied to an analyzer circuit (not shown in FIG. 7) which triggers an apnea alarm if the output signal from flip-flop 79 indicates that the amplitudes of the output signal of the integrator do not exceed the threshold value over a predetermined interval of time.

Figure 8:
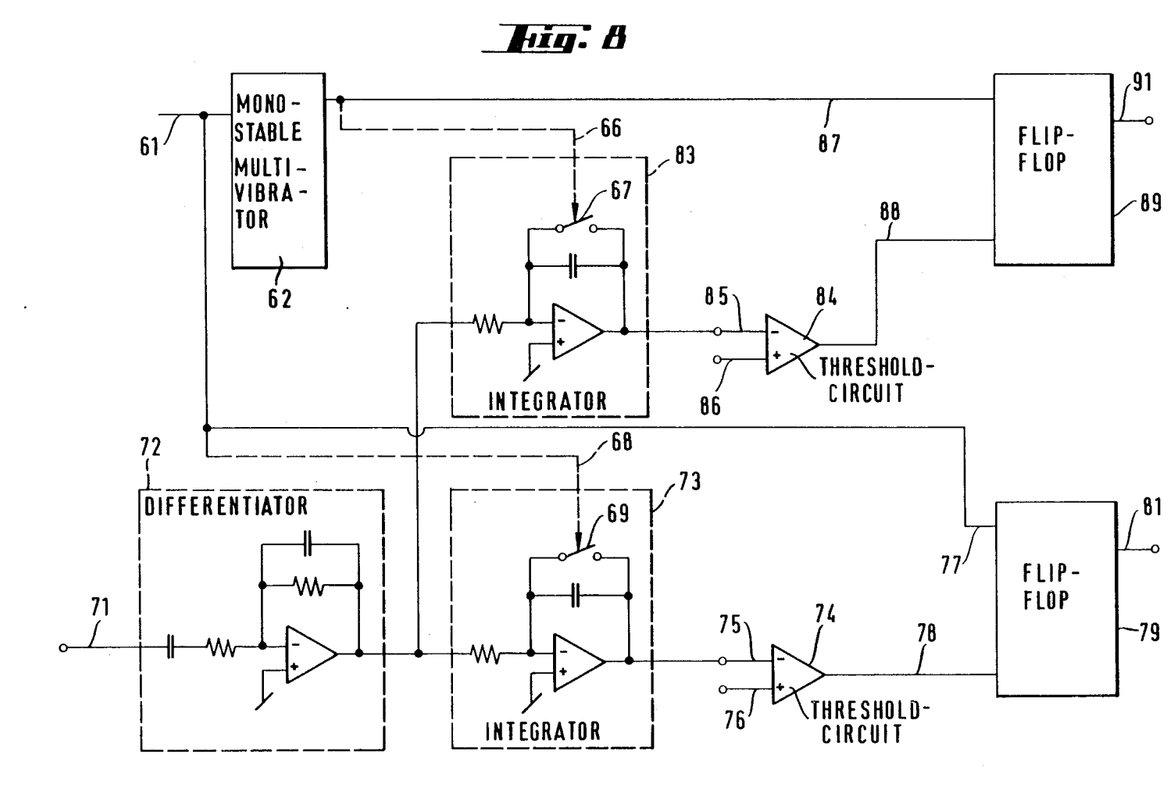
FIG. 8 is a modified version of the system shown in FIG. 7.

The electronic system described above allows the performance of the first embodiment of the method of the invention described above with reference to FIG. 3. FIG. 8 shows a more complete version of this system. This version allows performance of the preferred embodiment of the method according to the invention described above with reference to FIGS. 3 and 4.

The electronic system shown in FIG. 8 comprises all the elements shown in FIG. 7 and additionally the following elements:

a monostable multivibrator 62, to which there is fed via line 61 as an input signal pulses corresponding to respective QRS complexes. These same pulses control the closing of the switch 69 in the integrator 73 (via a control shown by broken line 68) and are also applied to the input 77 of the flip-flop 79.

an integrator 83 having the same configuration and in principle the same operation as the integrator 73. Resetting of integrator 83 to zero is effected by a switch 67 being closed for a short time. This switch is controlled (via a control denoted by a broken line 66) by the pulses delivered at the output of the monostable multivibrator 62. These pulses are delayed a certain amount with respect to the pulses representing the QRS complexes, the delay being, for example, 200 ms.

a threshold detector 84 having an input connected to the output of the integrator 83 by a line 85 and an input receiving a voltage corresponding to a threshold value via a line 86. The output signal of this detector is delivered over line 88. The operation of the threshold detector 84 is the same as that of the threshold detector 74.

A bistable type D flip-flop 89, the input signal of which is, on the one hand, the threshold detector output signal fed via line 88, and, on the other hand, the output signal of the monostable multivibrator 62 fed on line 87. The output signal of flip-flop 89 is fed via line 91 to an analyzer (not shown in FIG. 8). This analyzer triggers an apnea alarm only if the output signals of the flip-flops 79 and 89 indicate that the amplitudes of the output signals of the integrators 73 and 83 at the end of the respective integration intervals do not exceed the threshold value over a predetermined interval of time.

Figure 9:
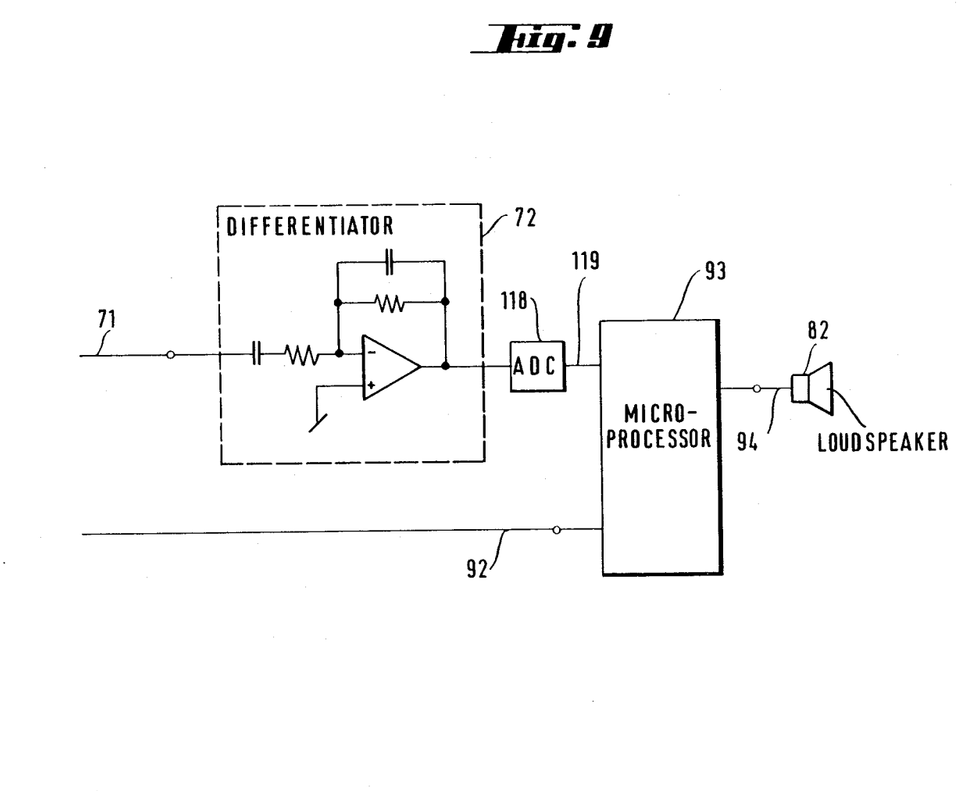
FIG. 9 shows a second embodiment of the systems of FIGS. 7 and 8.

FIG. 9 shows a second embodiment of the systems according to FIGS. 7 and 8. In the system shown in FIG. 9, the differentiating circuit 72 is retained but the other elements shown in FIGS. 7 and 8 are replaced by a microprocessor 93, which also carries out the function of the analyzer mentioned (but not shown) with reference to FIGS. 7 and 8. An analog-digital converter 118 is provided between the output of the differentiating circuit 72 and an input 119 of the microprocessor 93. Pulses corresponding to the QRS complexes and arriving via line 92 are fed to the "interrupt" input of the microprocessor 93. The latter performs integration operations by cumulating the values of the output signal of the differentiating circuit 72 every 1 ms in the integration intervals, with resetting to zero at the end of each of these intervals. The microprocessor 93 also compares the results of these integration operations with detection thresholds and, where applicable, triggers an alarm which is made audible by means of a loudspeaker 82 actuated by an output signal of the microprocessor 93 fed via line 94.

Figure 10:
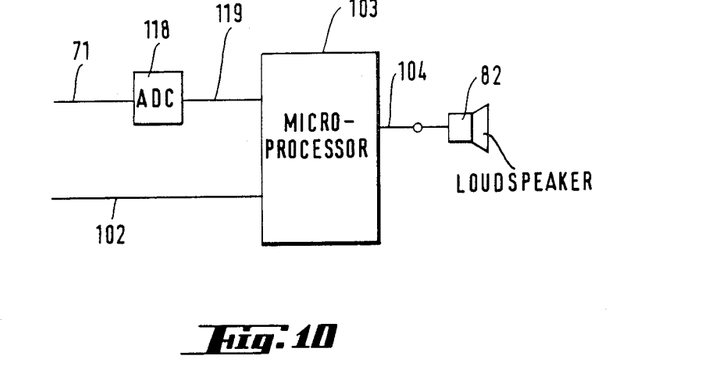
FIG. 10 shows a third embodiment of the systems of FIGS. 7 and 8.

FIG. 10 illustrates an entirely digital version of the system shown in FIG. 9. In this version, a microprocessor 103 also performs the function of the differentiating circuit 72. The respiratory signal delivered via line 71 is fed to the input of an analog-digital converter 118, the output of which is fed to the input 119 of the microprocessor. Pulses corresponding to the QRS complexes and arriving via line 102 are fed to the "interrupt" input of the microprocessor. As in the version of FIG. 9, a loudspeaker 82 is connected to the output 104 of the microprocessor and where applicable enables the apnea alarms triggered by the microprocessor to be made audible.

In the microprocessor 93 (FIG. 9) and 103 (FIG. 10), the value of a signal representing the first derivative of the respiratory signal is calculated every 1 ms by calculating the difference between two successive values of the respiratory signal.

Figure 11:
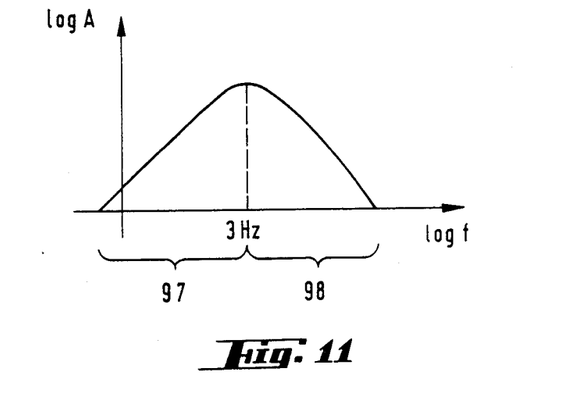
FIG. 11 illustrates a typical form of the amplitude-frequency characteristic curve of the differentiating circuit 72 in FIGS. 7-9 and 12.

FIG. 11 shows a typical form of the amplitude-frequency characteristic curve of the differentiating circuit 72 in FIGS. 7-9 and 12. The cut-off frequency at 3 hertz (Hz) shown in this figure is only a typical example. It is not an essential condition of the method.

Figure 12:
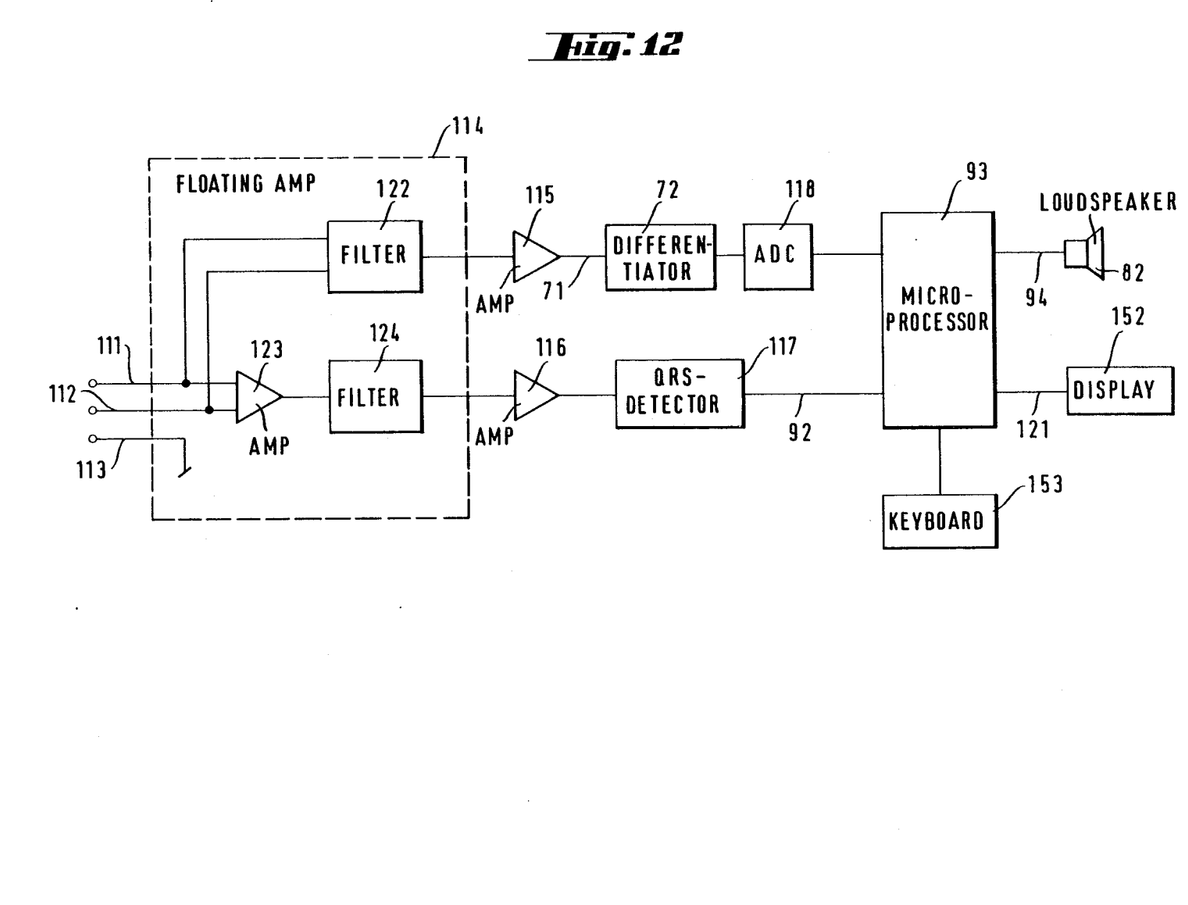
FIG. 12 is a block schematic diagram of an apparatus comprising the system shown in FIG. 9 for detecting apnea during monitoring of the respiratory signal.

FIG. 12 is a block schematic diagram of an apparatus comprising the system shown in FIG. 9 for apnea detection during monitoring of the respiratory signal. In addition to the elements of the system described above with reference to FIG. 9, the apparatus shown in FIG. 12 comprises the following elements:

a floating amplifier 114 whose inputs are connected to the electrodes 111, 112 and 113 shown in FIG. 1. One of the outputs of the amplifier 114 delivers a signal representing the patient's respiration. This signal is amplified by an amplifier 115 and the amplified signal is fed to the input of the differentiating circuit 72.

a second output of the floating amplifier 114 delivers a signal representing the patient's electrocardiogram. This signal is amplified by an amplifier 116 and the amplified signal is fed to the input of a circuit 117 for the detection of the QRS complexes. The output of the circuit 117 delivers pulses representing said complexes. The output of circuit 117 is connected to the "interrupt" input of the microprocessor 93 via a line 92.

a keyboard 153 is connected to one input of the microprocessor 93 for inputting certain parameters, e.g., the duration of the predetermined interval of time after which an apnea alarm is triggered in the method acording to the invention.

A digital display 152, e.g., a liquid crystal display, is connected via a line 121 to an output of the microprocessor 93. With this system it is possible to display alarm conditions, alarm causes, the contents of incident memories, and so on.

FIG. 12 illustrates an apparatus in which the respiratory signal and the signal representing the patient's ECG are produced with the same group of electrodes 111, 112, 113. In that case the floating amplifier 114 contains the means required for separating the respiratory signal from the ECG signal, e.g., a filter 122 for extracting the respiratory signal and the series circuit comprising an amplifier 123 and a filter 124 for extracting the ECG signal, in order to deliver these signals via separate outputs. Each of these signals, however, can be produced independently of the other, i.e., by separate means.

In the exemplified embodiments described above the differentiating circuit 72 may be replaced by filtering means having a similar transfer function.

Figure 13:
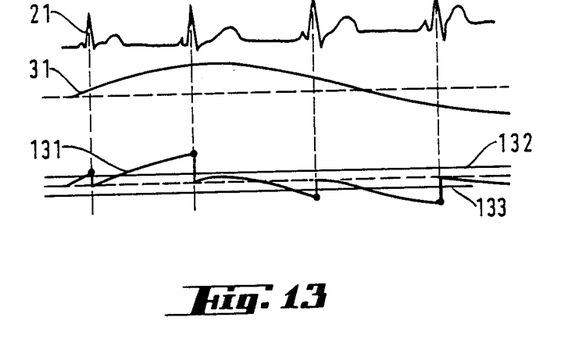
FIG. 13 illustrates a second embodiment of the method according to the invention by reference to some waveforms of the signals involved.

FIG. 13 illustrated a second embodiment of the method according to the invention. In this Figure a broken horizontal line represents the baseline of each of the signals shown. The incidence of each QRS complex of the electrocardiogram is shown by a vertical broken line. In this second embodiment, clamping of the respiratory signal is effected whenever a QRS complex is detected. A signal 131 is thus formed whose waveform corresponds to that of the respiratory signal in the intervals between successive QRS complexes, but which assumes the value zero whenever a QRS complex is detected. The values of the amplitude of the signal 131 at the times of incidence of the QRS complexes are compared with predetermined threshold values 132, 133. If the amplitudes of the signal 131 at said times do not exceed the threshold values 132 ad 133, respectively, over a predetermined interval of time, an alarm indicative of an apnea is triggered. In the opposite case illustrated in FIG. 13, in which the amplitudes of the signal 131 exceed said threshold values, the presence of normal respiration and hence the absence of apnea are confirmed.

Figure 14:
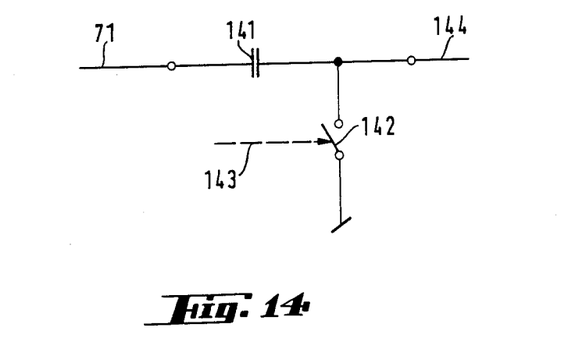
FIG. 14 diagrammatically illustrates a system for performing the method shown in FIG. 13.

FIG. 14 diagrammatically illustrates a system for performing the method illustrating in FIG. 13. This system enables analog clamping of the respiratory signal delivered via line 71 to be effected. The system comprises a connecting capacitor 141 and a switch 142. To provide clamping, the switch is closed for a short time on incidence of a QRS complex. Closing of the switch 142 is controlled by a pulse representing a QRS complex. This control is denoted by the broken lines 143 in FIG. 14. The clamped respiratory signal 131 is delivered via line 144 to an analyzer circuit (not show in FIG. 14), which triggers an apnea alarm if the amplitudes of the signal 131 do not exceed the threshold values 132, 133 over a predetermined interval of time. The function of the system shown in FIG. 14 may also be carried out by a microprocessor.

What is claimed is:

1. A method of monitoring waveforms representing the respiration of a patient and detecting waveforms having characteristics indicative of apnea, comprising processing a first electrical signal having a waveform representing the respiration of the patient and a second electrical signal representing the electrocardiogram of the patient, said method comprising:
    (a) forming a third signal which represents the first derivative of the first signal with respect to time,
    (b) forming a fourth signal which represents the integral of the third signal over first integration intervals, each of these intervals corresponding to the interval between two successive QRS complexes of the second signal,
    (c) comparing the amplitude of the fourth signal at the time of the incidence of each QRS complex which marks the end of one of the said integration intervals with a predetermined threshold value,
    (d) resetting to zero the fourth signal in synchronism with the incidence of each QRS complex on the second signal,
    (e) forming a fifth signal which represents the integral of the third signal over second integration intervals, each of which is offset by a predetermined interval of time with respect to one of the first integration intervals,
    (f) comparing the amplitude of the fifth signal at the time marking the end of each second integration interval with a predetermined threshold value,
    (g) resetting to zero the fifth signal at the end of each second integration interval, and
    (h) triggering an alarm only if the amplitudes of the fourth signal and the amplitudes of the fifth signal at the end of the respective integration intervals do not exceed the threshold value over a predetermined interval of time, said alarm being indicative of apnea.

2. An apparatus for monitoring the respiration of a patient, comprising means for forming a first electrical signal having a waveform representing the respiration of the patient and a second electrical signal representing the electrocardiogram of the patient, and means for detecting waveforms of the first signal having characteristics indicative of apnea, said means for detecting waveforms comprising:
    (a) means for forming a third signal representing the first derivative of the first signal with respect to time,
    (b) means for forming a fourth signal representing the integral of the third signal over first integration intervals, each of said intervals corresponding to the interval between two successive QRS complexes of the second signal,
    (c) means for comparing the amplitude of the fourth signal at the time of incidence of each QRS complex which marks the end of one of said integration intervals with a predetermined threshold value,
    (d) means for resetting the fourth signal to zero in synchronism with the incidence of each QRS complex on the second signal,
    (e) means for forming a fifth signal representing the integral of the third signal over second integration intervals, each of which is offset by a predetermined interval of time with respect to one of the first integration intervals,
    (f) means for comparing the amplitude of the fifth signal at the time marking the end of each second integration interval with a predetermined threshold value,
    (g) means for resetting the fifth signal to zero at the end of each second integration interval, and
    (h) means for triggering an alarm if the amplitudes of the fourth signal and the amplitudes of the fifth signal at the end of the respective integration intervals do not exceed the threshold value over a predetermined interval of time, said alarm being indicative of apnea.

3. An apparatus according to claim 2, wherein the means for forming the third signal are filtering means having a frequency attenuation characteristic similar to that of a differentiating circuit.

* * * * *